United States Patent [19]

Friary

[11] Patent Number: 4,897,391

[45] Date of Patent: Jan. 30, 1990

[54] TRICYCLIC ANTI-ALLERGY, ANTIINFLAMMATORY AND ANTI-HYPERPROLIFERATIVE COMPOUNDS

[75] Inventor: Richard J. Friary, West Orange, N.J.

[73] Assignee: Schering Corporation, Kenilworth, N.J.

[21] Appl. No.: 208,304

[22] Filed: Jun. 17, 1988

[51] Int. Cl.$^4$ .................. A61K 31/55; A61K 31/33; C07D 455/04
[52] U.S. Cl. .................................. 514/183; 514/214; 514/294; 540/479; 540/586; 546/94
[58] Field of Search .............. 546/94; 540/479, 586; 514/183, 214, 294

[56] References Cited

U.S. PATENT DOCUMENTS 3,824,244 7/1974 Houlihan et al. ............... 546/94 X
4,052,508 10/1977 Anderson et al. ............. 546/101 X

FOREIGN PATENT DOCUMENTS 54-39097 3/1979 Japan ........................... 546/94
047485 4/1975 United Kingdom .

OTHER PUBLICATIONS

Janssen, P. et al., Arzneim-Forsch. 15, 104–117(1965), Reprint, p. 3.
Coppola, G., J. Heterocyclic Chem., 18:767 (1980).
Shiraiwa, M. et al., Chem. Pharm. Bull. 31:2275 (1983).
Chem. Abstrs. 62:16179e (1965) [Desai, H. et al., J. Indian Chem Soc., 41(12), 821–9(1964)].
Desai, H. et al., J. Indian Chem. Soc., 41 (12), 821 (1964).
Derwent Abstract of DT 2,448,287, 4/17/75.

*Primary Examiner*—Richard A. Schwartz
*Attorney, Agent, or Firm*—Edward H. Mazer; James R. Nelson; Stephen I. Miller

[57] ABSTRACT

Isoquinolinone and isothiochromone derivatives of the general formula

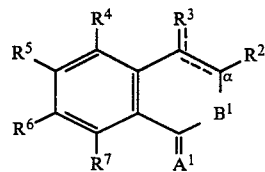

1.0 are disclosed. These compounds display anti-allergy, antiinflammatory and anti-hyperproliferative activity, which makes them useful for treating related disorders.

18 Claims, No Drawings

TRICYCLIC ANTI-ALLERGY, ANTIINFLAMMATORY AND ANTI-HYPERPROLIFERATIVE COMPOUNDS

BACKGROUND OF THE INVENTION

The present invention relates to novel isoquinolinone and isothiochromone compounds that possess anti-allergy activity.

British Patent 047485 discloses compounds of the general formula

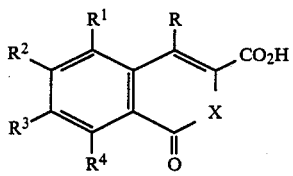

wherein:
X is O, S or NH;
R is H or alkyl; and
$R^1$, $R^2$, $R^3$ and $R^4$ are the same or different and each is chosen from H, halogen, alkyl, alkoxy, aryl, aralkyl, acyloxy, heterocyclic or $CO_2H$. These compounds are disclosed as having anti-allergy activity, inhibiting known antigen-antibody reactions and being useful in the prophylaxis and therapy of diseases caused by allergic or immunological reactions.

Coppola, *J. Heterocyclic Chem.* 1981 18, 767, discloses compounds of the general formula

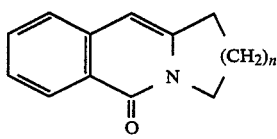

wherein n can be 1, 2 or 3. No activities for these compounds are disclosed or discussed.

Shiraiwa et al., *Chem. Pharm. Bull.* 1983, 31, 2275, discloses compounds of general formulas

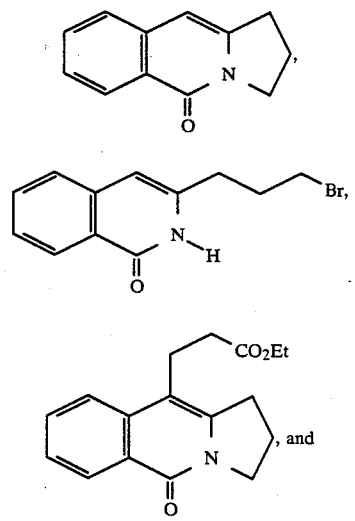

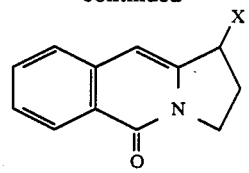

wherein X is Br or OH. No activities for these compounds are disclosed or discussed.

*Chem. Absts.* 1965, 62, 16179e, discloses compounds of the general formula

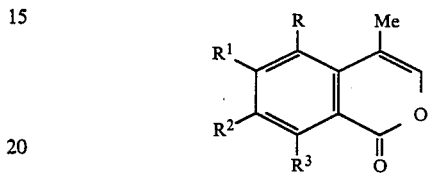

wherein
R is H, OH or $OCH_3$;
$R^1$ is H or $CH_3$;
$R^2$ is H or $OCH_3$; and
$R^3$ is H or $CH_3$.
No activities for these compounds are disclosed or discussed.

SUMMARY OF THE INVENTION

A compound of formula 1.0

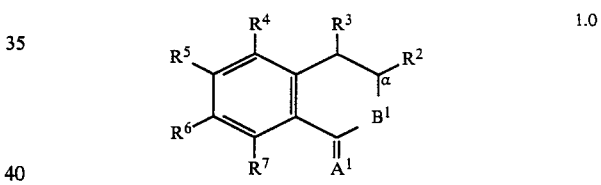

or a pharmaceutically acceptable salt or solvate thereof, wherein:
the dotted lines represent optional double bonds, one of which may be present in any given compound and when both are absent, the results are single bonds terminating at the α carbon and at the two substituents being represented by $R^3$ as defined below;
$A^1$ is selected from O, S, $=N(SO_2)$-alkyl, $=N(SO_2)$-aryl, $=N(SO_2)$-heteroaryl, $=NC\equiv N$, $=N(CO_2)$-aryl, $=N(CO_2)$-heteroaryl, $=NCO_2$-alkyl or $=N$-alkyl;
$B^1$ is selected from $NR^1$ or S;
$R^1$ is selected from H, alkyl, arylmethyl, or heteroarylmethyl, or, together with $R^2$, represents $(CH_2)_a$, in which a is 3, 4, 5, or 6 so as to form a heterocyclic ring of atoms;
$R^2$ may also represent a group selected from H, alkyl, aryl, heteroaryl or cycloalkyl;
$R^3$ is selected from H, alkyl, arylmethyl, aryl, heteroaryl, OH, -O-alkyl, -O-acyl, -O-aroyl or -O-heteroaroyl when the dotted line terminating at $R^3$ is absent and the double bond terminating at the α carbon is present; or $R^3$ represents $CHR^0$ where $R^0$ is selected from H, alkyl, heteroaryl, arylmethyl or together with $R^2$ may represent $(CH_2)_b$ in which b is 3, 4, 5 or 6 so as to form a carbocyclic ring, when the dotted line terminating at the α carbon is absent and the dotted line terminating at $R^3$ is present and represents a double bond; or $R^3$ represents two substituents selected from OH and aryl, OH and alkyl, or OH and arylmethyl when both dotted lines terminating at $R^3$ and at the α carbon are absent, with the proviso that the alkyl substituent may combine with $R^2$ to represent $(CH_2)_b$ in which b is 3, 4, 5 or 6 so as to form a carbocyclic ring as described above; or $R^3$ together with $R^2$ represents $(CH_2)_b$ in which b is 3, 4, 5 or 6, so as to form a carbocyclic ring in which the dotted line ending at the α carbon may be present as described above;

$R^4$ and $R^6$ may be the same or different and each is independently selected from H, halo, —$CF_3$, —$NO_2$, —$OR^8$, —O—acyl, —$OC(O)CH_2N(R^8)_2$, —$OC(O)CH_2OH$, —O—aroyl, —O—heteroaroyl, —$OC(O)N(R^8)_2$, —$SR^8$, —S—acyl, —$SC(O)CH_2N(R^8)_2$, —$SC(O)CH_2OH$, —S—aroyl, —S—heteroaroyl, —$SC(O)N(R^8)_2$, —$SO_2$—alkyl, —$SO_2$—aryl, —$SO_2$—aralkyl, —$N(R^8)_2$, —$N(R^8)$—acyl, —$N(R^8)C(O)CH_2N(R^8)_2$, —$N(R^8)C(O)CH_2OH$, —$N(R^8)$—aroyl, —$N(R^8)$—heteroaroyl, —$N(R^8)C(O)N(R^8)_2$, —$CO_2R^8$, —$C(O)N(R^8)_2$, —$CO_2$—alkyl, —$CO_2$—aryl or —$CO_2$—aralkyl, with the proviso that at least one of $R^4$ and $R^6$ is selected from SH, OH, —$NHR^8$, —NH—acyl, —$NHC(O)CH_2N(R^8)_2$, —$HNC(O)CH_2OH$, —NH—aroyl, —NH—heteroaroyl, —$NHC(O)N(R^8)_2$, —O—acyl, —$OC(O)CH_2N(R^8)_2$, —$OC(O)CH_2OH$, —O—aroyl, —O—heteroaroyl, —$OC(O)N(R^8)_2$, —S—acyl, —$SC(O)CH_2N(R^8)_2$, —$SC(O)CH_2OH$, —S—aroyl, —S—heteroaroyl, —$SC(O)N(R^8)_2$ or $N(R^8)C(O)N(R^8)_2$;

$R^5$ and $R^7$ may be the same or different and each is independently selected from H, halo, —$CF_3$, —$NO_2$, alkyl, aryl, arylmethyl, heteroaryl, (heteroaryl)methyl, —$S(O)_c$—alkyl or —$S(O)_c$—aryl (in both of which c is 0, 1, or 2), —$OR^8$, —O—acyl, —$OC(O)CH_2N(R^8)_2$, —$OC(O)CH_2OH$, —O—aroyl, —O—heteroaroyl, —$OC(O)N(R^8)_2$, —$SR^8$, —S—acyl, —$SC(O)CH_2N(R^8)_2$, —$SC(O)CH_2OH$, —S—aroyl, —S—heteroaroyl, —$SC(O)N(R^8)_2$, —$N(R^8)_2$, —$N(R^8)$—acyl, —$N(R^8)C(O)CH_2N(R^8)_2$, —$N(R^8)C(O)CH_2OH$, —$N(R^8)$—aroyl, —$N(R^8)$—heteroaroyl, —$N(R^8)C(O)N(R^8)_2$, —$CO_2R^8$ or —$C(O)N(R^8)_2$; and each $R^8$ is independently selected from H or alkyl.

In a preferred embodiment of the invention, $B^1$ is $NR^1$ and $A^1$ is 0.

In another preferred embodiment of the invention, $R^1$ and $R^2$ together represent $(CH_2)_4$ so as to represent a heterocyclic ring and $R^3$ is alkyl.

In another preferred embodiment of the invention $R^4$ and $R^6$ may be the same or different and each is independently selected from H, —$OC(O)CH_3$, OH, O—$Na^{30}$, —$OCH_3$ or —$OC(O)CH_2N(R^8)_2$, with the proviso that at least one of $R^4$ and $R^6$ is selected from OH, —$OC(O)CH_3$ or —$OC(O)CH_2N(R^8)_2$.

In another preferred embodiment of the invention, $R^5$ and $R^7$ may be the same or different and each is independently selected from H, OH, —O—acyl or —$OC(O)CH_2NH_2$, more preferably H or —$OC(O)CH_3$.

Preferred species falling within the scope of formula 1.0 include:

1,2,3,4-tetrahydro-8,10-dihydroxy-11-6H-benzo[b]quinolizin-6-one,
1,2,3,4-tetrahydro-8,10,11-trihydroxy-6H-benzo[b]quinolizin-6-one,
5,7-dihydroxy-4-phenyl-1(2H)-dihydroisoquinolinone,
1,2,3,4-tetrahydro-9,10-dihydroxy-11-methyl-6H-benzo[b]quinolizin-6-one,
1,3,4,5-tetrahydro-8,10-dihydroxy-phenanthridin-6(2H)-one,
1,2,3,4,11,11a-hexahydro-8,10,11-trihydroxy-11-phenyl-6H-benzo[b]quinolizin-6-one,
2,3-dihydro-7,9-dihydroxy-10-phenylpyrrolo[1,2-b]isoquinolin-5(1H)-one,
9,10-bis(acetyloxy)-1,2,3,4,11,11a-hexahydro-11-methylene-6H-benzo[b]quinolizin-6-one,
8,10-bis(acetyloxy)-1,2,3,4,-tetrahydro-11-phenyl-6H-benzo[b]quinolizin-6-one,
8,10,11-tris(acetyloxy)-1,2,3,4-tetrahydro-6H-benzo[b]quinolizin-6-one,
8,10-bis(2,2-dimethyl-1-oxopropoxy)-11-methyl-1,3,4,6-tetrahydro-6H-benzo[b]quinolizin-6-one,
7,8-bis(acetyloxy)-1,2,3,4-tetrahydro-11-methyl-6H-benzo[b]quinolizin-6-one
8-acetyloxy-1,2,3,4-tetrahydro-11-methyl-6H-benzo[b]quinolizin-6-one,
9,10-bis(acetyloxy)-1,2,3,4-tetrahydro-11-methyl-6H-benzo[b],-QUINOLIZIN-6-one,
7,9-bis(acetyloxy)-2,3-dihydro-10-methyl-pyrrolo[1,2-b]isoquinolin-5(1H)-one,
5,7-bis(acetyloxy)-4-methyl-1(2H)-isoquinolinone,
5,7-bis(acetyloxy)-4-phenyl-1(2H)-isoquinolinone,
5,7-bis(acetyloxy)-3-methyl-4-phenyl-1(2H)-isoquinolinone,
5,7-bis(acetyloxy)-2,3-dimethyl-4-phenyl-1(2H)-isoquinolinone,
8,10-bis(acetyloxy)-1,3,4,5,6-tetrahydro-6(2H)-phenanthridinone,
8,10-bis(acetyloxy)-1,2,3,4-tetrahydro-11-methyl-6H-benzo[b]quinolizin-6-one,
7,9-bis(acetyloxy)-2,3-dihydro-10-phenyl-6H-pyrrolo[1,2-b]isoquinolin-5(1H)-one,
8-acetyloxy-1,2,3,4,11,11a-hexahydro-11-hydroxy-11-methyl-6H-benzo[b]quinolizin-6-one,
1,2,3,4-tetrahydro-8,10-dihydroxy-11-methyl-6H-benzo[b]quinolizin-6-one, disodium salt
8,10-bis[(aminoacetyl)oxy]-11-methyl-1,2,3,4-tetrahydro-6H-benzo[b]quinolizine-6-one,
8,10-bis[(aminoacetyl)oxy]-11-methyl-1,2,3,4-tetrahydro-6H-benzo[b]quinolizine-6-one dihydrochloride,
5,7-bis(acetyloxy)-2,3-dimethyl-4-phenyl-1(2H)isoquinolin-1-one,
8,10-bis(acetyloxy)-1,3,4,5-tetrahydro-5-methyl-6(2H)-phenanthridinone,
8,10-bis(methoxy)-1,2,3,4-tetrahydro-11-methyl-6H-benzo[b]quinolizin-6-one, or
1,2,3,4-tetrahydro-8,10-dihydroxy-6H-benzo[b]quinolizin-6-one.

Preferred specifies are compounds selected from the following compounds A through E, wherein the structure and name is providing for each:

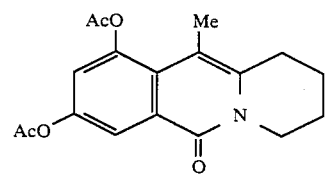

A 8,10-bis(acetyloxy)-1,2,3,4-tetrahydro-11-methyl-6H-benzo[b]quinolizin-6-one;

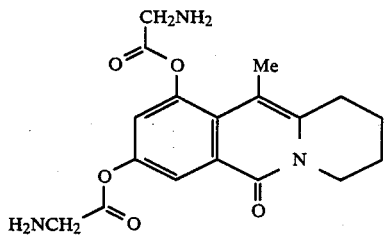
B 8,10-bis[(aminoacetyl)oxy]-11-methyl-1,2,3,4-tetrahydro-6H-benzo[b]quinolizin-6-one;

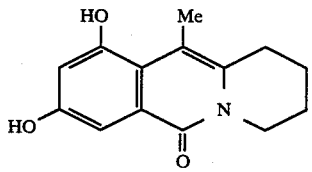
C 1,2,3,4-tetrahydro-8,10-dihydroxy-11-methyl-6H-benzo[b]quinolizin-6-one;

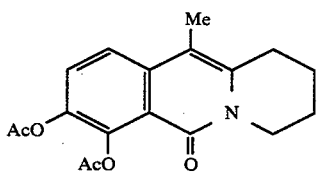
D 7,8-bis(acetyloxy)-1,2,3,4-tetrahydro-11-methyl-6H-benzo[b]quinolizin-6-one;

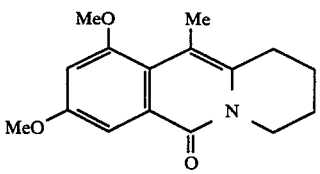
E 8,10-bis(methoxy)-1,2,3,4-tetrahydro-11-methyl-6H-benzo[b]quinolizin-6-one;
wherein Ac represents acetyl and Me represents $CH_3$, or from a pharmaceutically acceptable salt or solvate thereof.

The invention also includes a pharmaceutical composition which comprises a compound having a structural formula 1.0 in combination with a pharmaceutically acceptable carrier and methods for treating allergy, inflammation and/or hyperproliferative skin disease in a mammal that comprise administering an anti-allergy, antiinflammation and/or anti-hyperproliferative effective amount respectively of the above defined compounds to said mammal.

DETAILED DESCRIPTION OF THE INVENTION

Certain compounds of formula 1.0 may exist in different isomeric as well as conformational forms. The invention contemplates all such isomers both in pure form and in admixture, including racemic mixtures.

The compounds of formula 1.0 can exist in unsolvated as well as solvated forms, including hydrated forms, e.g., hemihydrate. In general, the solvated forms, with pharmaceutically acceptable solvents such as water, ethanol and the like, are equivalent to the unsolvated forms for purposes of the invention.

Certain compounds of formula 1.0 will be acidic in nature, e.g. those compounds which possess a carboxylic or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of formula 1.0 also form pharmaceutically acceptable salts, e.g., acid addition salts and quaternary ammonium salts. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to product a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g., by reaction of a tertiary amino group in a compound of formula 1.0 with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

When utilized herein, the terms below, unless otherwise indicated, have the following scope:

halo—represents fluoro, chloro, bromo and iodo;
alkyl—represents straight or branched carbon chains, which contain from 1 to 6 carbon atoms unless otherwise specified;
cycloalkyl—represents a saturated carbocyclic ring having from 3 to 6 carbon atoms;
alkenyl—represents straight or branched carbon chains having at least one carbon to carbon double bond and preferably having from 2 to 6 carbon atoms;
cycloalkenyl—represents a carbocyclic ring having from 5 to 8 carbon atoms and at least one carbon to carbon double bond in such ring;
alkynyl—represents straight or branched carbon chains having at least one carbon to carbon triple bond and preferably having from 2 to 6 carbon atoms;
cycloalkynyl—represents a carbocyclic ring having at least 8 carbon atoms, preferably 8 to 15 carbon atoms and at least one carbon to carbon triple bond in such ring;
aralkyl—represents an alkyl as defined above in which an aryl group as defined below is substituted for one of the alkyl H atoms;
heteroaralkyl—represents an aralkyl as defined above in which the aryl group is a heteroaryl group as defined below;

aryl—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted with 1 to 3 Y groups, each independently selected from halo, alkyl, hydroxy, alkoxy, phenoxy, amino, alkylamino, dialkylamino. Preferred aryl groups are

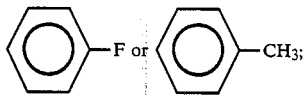

heteroaryl (including the heteroaryl portion heteroarylmethyl)—represents cyclic groups having at least one O, S and/or N interrupting a carbocyclic ring structure and having a sufficient number of delocalized pi electrons to provide aromatic character, with the aromatic heterocyclic groups preferably containing from 2 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc. Preferred heteroaryl groups are pyridyl, 2- or 3-furyl, 2- or 3-thienyl, 2-, 4- or 5-imidazolyl or 7-indolyl;

acyl—represents -C(O)-alkyl, -C(O)-alkenyl, -C(O)-alkynyl, -C(O)-cycloalkyl, -C(O)-cycloalkenyl or -C(O)-cycloalkynyl;

aroyl—represents C(O)-aryl wherein aryl is a defined above, preferably

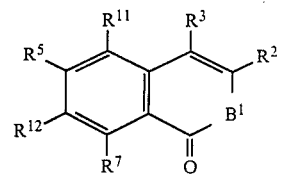

and heteroaroyl—represents -C(O)-heteroaryl, wherein heteroaryl is as defined above and preferably the heteroaryl group is 2, 3 or 4-pyridyl, 2- or 3-furyl, 2-or 3-thienyl, 2-, 4-, or 5-imidazolyl or 7-indolyl.

Below, general methods for preparing the compounds of the present invention are described.

Compounds of general formula 1.0 are prepared by processes (a) through (i) below, wherein $R^1$, $R^2$, $R^3$, $R^4$, $R^5$, $R^6$, $R^7$, $R^8$, $A^1$, $B^1$, and the dotted lines are as defined above and wherein $R^a$, $R^b$, $R^c$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $L^1$, $L^2$, $L^3$, $A^2$, and $B^2$ are as defined below.

Compounds of formula 1.2 may be produced from the same starting material, viz., a compound of formula 2.1, using the same method, which is shown in process (b) below.

(a) A compound of formula 2.1, which may be obtained from process (j) or (k) below, is allowed to react with a base to produce a compound of formula 1.1:

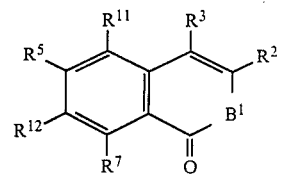

Any base which will not cleave the bond linking $B^1$ to the adjacent carbonyl is suitable and may be used, e.g., $M_2^+CO_3^{-2}$ or $M^+$—O—alkyl, wherein $M^+$ is $Li^+$, $Na^+$, or $K^+$, preferably $Na^+$. The reaction may be carried out in a polar solvent, which may be, e.g., dimethylsulfoxide, N,N-dimethylformamide, water, alcohol, or a mixture of the last two, and the solvent is preferably anhydrous ethanol or anhydrous methanol. Also, the reaction may be carried out at any suitable temperature, e.g., from 0° C. to the reflux temperature of the solvent used, preferably at the latter temperature. In formula 2.1, at least one of $R^9$ and $R^{10}$ represents $OR^a$, $SR^a$, or $NHR^b$, wherein $R^a$ is hydrogen, acyl, aroyl, heteroaroyl and $R^b$ is —$SO_2$—alkyl, —$SO_2$—aryl, —$SO_2$—aralkyl, —$CO_2$—alkyl, —$CO_2$—aryl, or —$CO_2$aralkyl, and the other may represent a suitable precursor to the desired $R^4$ or $R^5$ group. In formula 1.1 and elsewhere herein, at least one of $R^{11}$ and $R^{12}$ represents OH, SH, or $NHR^b$, and the other may represent a suitable precursor to the desired $R^4$ or $R^5$ group.

(b) A compound of formula 2.1, which may be obtained from process (j) or (k) below, is allowed to react with a base to produce a compound of formula 1.2:

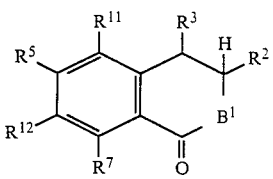

Any base which will not cleave the bond linking $B^1$ to the adjacent carbonyl is suitable and may be used, e.g., $M_2^+CO_3^{-2}$ or $M^+$—O—alkyl, wherein $M^+$ is $Li^+$, $Na^+$, or $K^+$, preferably $Na^+$. The reaction may be carried out in a polar solvent, which may be, e.g , dimethylsulfoxide, N,N-dimethylformamide, water, alcohol, or a mixture of the last two, and the solvent is preferably anhydrous ethanol or anhydrous methanol. Also, the reaction may be carried out at any suitable temperature, e.g., from 0° C. to the reflux temperature of the solvent used, preferably at the latter temperature.

Note that, depending on the nature of $R^3$, the reactions of processes (a) and (b) may produce mixtures of compounds and that the products may be separated by conventional techniques well known to those skilled in the art.

(c) A compound of formula 2.2, which may be obtained from process (j) or (k) below, is allowed to react with a suitable acid to produce a compound of formula 1.3:

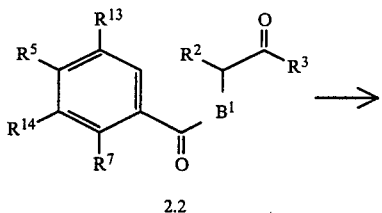

2.2

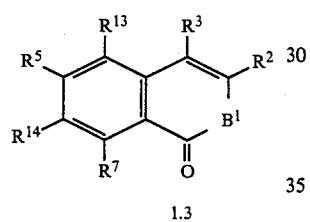

1.3

Examples of acid catalysts for the reaction are toluenesulfonic acid, methansulfonic acid, trifluoromethylsulfonic acid and the like, preferably, trifluoroacetic acid. The reaction may be carried out with a suitable solvent, e.g, a halocarbon, a hydrocarbon, an ethereal solvent, or an alcoholic solvent, such as dichloromethane, chloroform, benzene, toluene, diethyl ether, ethanol, or carbon tetrachloride, or without any solvent except for an excess of the acid, e.g., trifluoroacetic acid. Carbon tetrachloride is the preferred solvent. The reaction may be carried out at any suitable temperature, e.g., from 0° C. to the boiling point of the solvent employed, and is preferably the latter.

In formulas 2.2 and 1.3, $R^{13}$ and $R^{14}$ represent $OR^c$ or $SR^c$ in which $R_c$ is hydrogen, alkyl, aryl, or aralkyl.

(d) A compound of formula 2.3 (formula 2.1 wherein $R^3$ is $L^1$) is allowed to react with a base to produce a compound of formula 1.4:

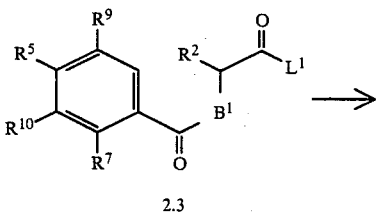

2.3

-continued

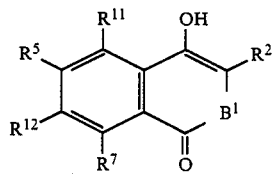

1.4

Any base which will not cleave the bond linking $B^1$ to the adjacent carbonyl is suitable and may be used, e.g., $M_2^+CO_3^{-2}$ or $M^+{}^-O$—alkyl, wherein $M^+$ is $Li^+$, $Na^+$, or $K^+$, preferably $Na^+$. The reaction may be carried out in a polar solvent, which may be, e.g., dimethylsulfoxide, N,N-dimethylformamide, water, alcohol, or a mixture of the last two, and the solvent is preferably anhydrous ethanol or anhydrous methanol. Also, the reaction may be carried out at any suitable temperature, e.g., from 0° C. to the reflux temperature of the solvent used, preferably at the latter temperature.

In formula 2.3, $L^1$ represents any suitable leaving group, e.g., O-alkyl, O-aryl, O-aralkyl, S-alkyl, S-aryl, or S-aralkyl.

(e) A compound of formula 1.1, which may be obtained from process (a) above, is allowed to react with an esterifying or amidating agent to produce a compound of formula 1.5:

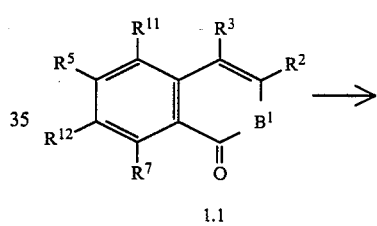

1.1

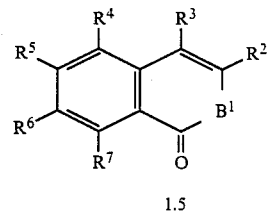

1.5

Suitable esterifying or amidating agents are anhydrides or chlorides of carboxylic acids, and, when the agent is an anhydride or a chloride, it is desirable to employ a tertiary amine base like triethyl amine, diisopropylethyl amine, 4-dimethyl- or 4-pyrrolidinylaminopyridine, or, preferably, pyridine. Other suitable esterifying or amidating agents are a combination of 1,1'-carbonyldiimidazole and 4-dimethylaminopyridine. The preferred agent is a carboxylic acid anhydride combined with pyridine.

The reaction may be carried out in any suitable solvent, e.g., chloroform, dichloromethane, N,N-dimethylformamide, benzene, toluene, and the like. A preferred solvent is chloroform. The reaction may be carried out without any solvent if the esterifying or amidating agent and base are a carboxylic acid anhydride and, e.g., pyridine.

The reaction may be carried out at any suitable temperature e.g., from 0° C. to the reflux temperature of the solvent used, preferably at the latter temperature. If no solvent, except for an excess of a carboxylic acid anhydride combined with a base like pyridine, is used, then the reaction may be carried out at temperatures ranging from 25° C. to 75° C. The preferred temperature is then about 25° C.

(f) A compound of formula 1.6 (formula 1.5 wherein $B^1$ is $NR^1$ and $R^1$ is H) is allowed to react with an alkylating agent and a base to produce a compound of formula 1.7:

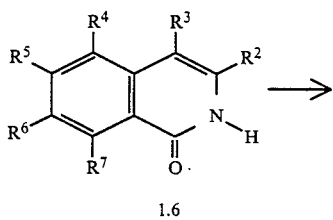

1.6

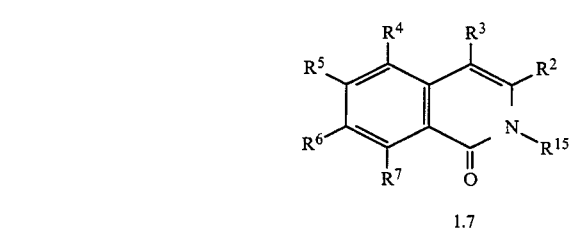

1.7

Suitable alkylating agents are $R^{15}L^3$, in which $L^3$ represents a suitable leaving group such as halogen, $-OS(O)_2CH_3$, $-OS(O)_2C_6H_4-CH_3-p$, $-OS(O)_2CF_3$, and the like. A preferred leaving group is I, and use of the alkylating agent in excess is preferred. Suitable bases are sodium or potassium hydride, $M^+ {}^-O-$alkyl, in which $M^+$ represents $Na^+$, $K^+$, and $Li^+$, lithium diisopropylamide, and lithium hexamethyldisilazide. The preferred base is sodium hydride.

The reaction may be carried out in a solvent, and a most preferred solvent is N,N-dimethylformamide. Other solvents are also suitable, and include dimethylsulfoxide, alcohols, preferably tert.-butanol, and ethers, preferably diethyl ether, 1,4-dioxane, tetrahydrofuran, and 1,2-dimethoxyethane.

The reaction is carried out at any suitable temperature, e.g., from 0° C. to the boiling point of the solvent employed, and the preferred temperature is about 25° C.

$R^{15}$ represents alkyl, aralkyl, or heteroaralkyl. (g) A compound of formula 1.8 (formula 1.0 wherein $A^1$ is (O) is allowed to react with a sulfurating agent to produce a compound of formula 1.9:

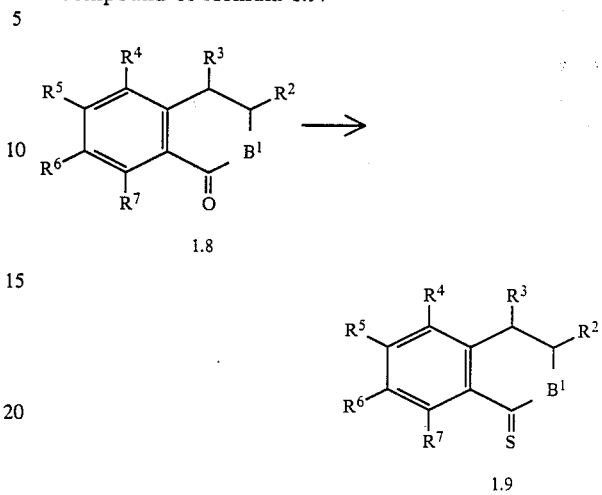

Suitable sulfurating agents include $P_2S_5$ and Lawesson's reagent, which has the structure below:

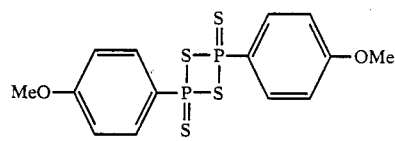

The reaction takes place at elevated temperature, preferably in solvents like pyridine and toluene, as well as in other suitable solvents.

(h) A compound of formula 1.8 (formula 1.0 wherein $A^1$ is (O) is allowed to react with an activating agent, and then with a nitrogen nucleophile, to produce a compound of formula 1.10:

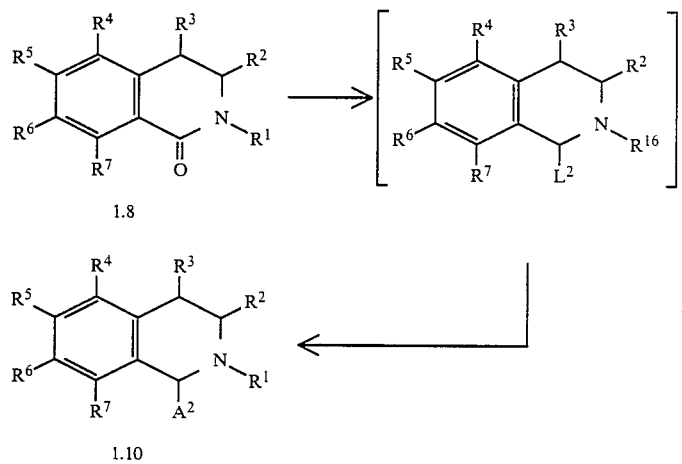

Suitable activating agents include thionyl chloride, oxalyl chloride, $PCl_3$, and $POCl_3$. Suitable nitrogen nucleophiles are exemplified by $H_2A^2$, wherein the group $A^2$ is as defined below. Both steps of the transformation may be carried out in a solvent, and a suitable solvent is chosen from among dichloromethane, chloroform, carbon tetrachloride, 1,2-dichloroethane, benzene, toluene, and the like.

In a first step, the activating agent is allowed to react with a compound of formula 1.8, typically at a low temperature, e.g., from −20 to +25° C., and a preferred temperature for this step is about 0° C. When the reaction of the first step, yielding an intermediate compound, is complete, then the second step is begun.

In the second step, the intermediate compound may be treated in situ with the nitrogen nucleophile, which produces a compound of formula 1.10. The temperature ranges from about 0° C. to the boiling point of the solvent employed, and preferably is between 25 and 50° C.

In the intermediate (bracketed) compounds above, $L^2$ represents a leaving group such as halogen, —OS(O)$_2$CH$_3$, —OS(O)$_2$C$_6$H$_4$CH$_3$—p, —OS(O)$_2$CF$_3$, —S—alkyl, —SO$_2$—alkyl, and the like, and $R^{16}$ represents either the s-electrons of the attached N-atom, or a positive charge and $R^{15}$. In formula 1.10, $A^2$ represents —NSO$_2$—alkyl, —NSO$_2$—aryl, —NSO$_2$—het— eroaryl, NC≡N, —NCO$_2$—alkyl, —NCO$_2$—aryl, —NCO$_2$—heteroaryl, or N—alkyl.

(i) To produce a compound of formula 1.12, a compound of formula 1.11, which is obtained according to process (d) above, is allowed to react with gaseous hydrogen under pressure and in the presence of a noble metal catalyst. A solvent is used for the reaction.

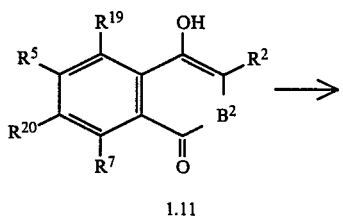

1.11

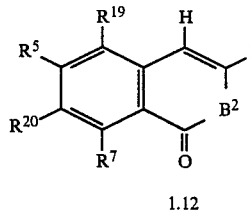

1.12

The hydrogen pressure used for the reaction ranges from atmospheric to 300 psi, and is preferably about 60 psi. The catalyst used is selected from among palladium-on-carbon, platinum-on-carbon, platinum oxide-on-carbon, and rhodium-on-alumina, and is preferably rhodium-on-alumina, as disclosed by *J. Org. Chem.* (1962, 27 2288). The amount of catalyst and proportion of the active ingredient, e.g., rhodium, to diluent, e.g., alumina, are chosen according to the judgement of the operator, as is the time of reaction. The solvent for the reaction is an alcohol, typically tert.-amylalcohol or tert.-butanol, and preferably tert.-butanol, containing an alkyl carboxylic acid, preferably acetic acid. The preferred ratio of solvent to acid is about 220 parts to 1 part, by volume, and other ratios, e.g., 10 parts to 1 part, may be used.

In formula 1.11, $R^{19}$ and $R^{20}$ represent OH, —O—acyl, —O—alkyl, NH—acyl, —NHSO$_2$—alkyl, and the like. In formulas 1.11, 1.12, 3.0, and 6.0, $B^2$ represents $NR^1$.

As is apparent to one skilled in the art, certain final compounds can be transformed into other final compounds by standard reactions well known in the art.

Compounds of general formula 2.0 are prepared by processes (j)–(m) below. In formulas 4.0, 2.1, 2.4, and elsewhere herein, $R^{17}$ and $R^{18}$ respectively represent $R^9$ and $R^{10}$, $R^{13}$ and $R^{14}$, or they represent $R^{19}$ and $R^{20}$.

(j) A compound of formula 4.0 is allowed to react with a compound of formula 5.1 and a base to produce a compound of formula 2.1:

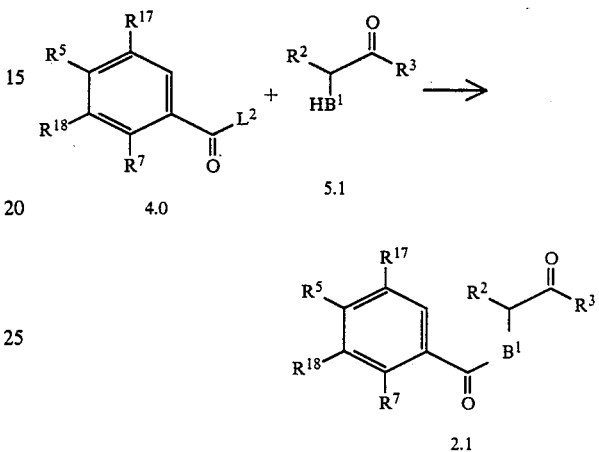

The base is typically a tertiary amine base such as pyridine, triethylamine, or diisopropyethylamine, preferably diisopropyethylamine. A suitable solvent for the reaction is chosen from among dichloromethane, chloroform, carbon tetrachloride, 1,2-dichloroethane, benzene, toluene, and the like. The reaction is preferably carried out at temperatures ranging from 0° C. to 25° C.; a wider temperature range may also be employed, e.g., −10 to 50° C.

(k) A compound of formula 3.0 is allowed to react with an oxidizing agent to produce a compound of formula 2.4 (formula 2.1 wherein $B^1$ is $NR^1$ or O):

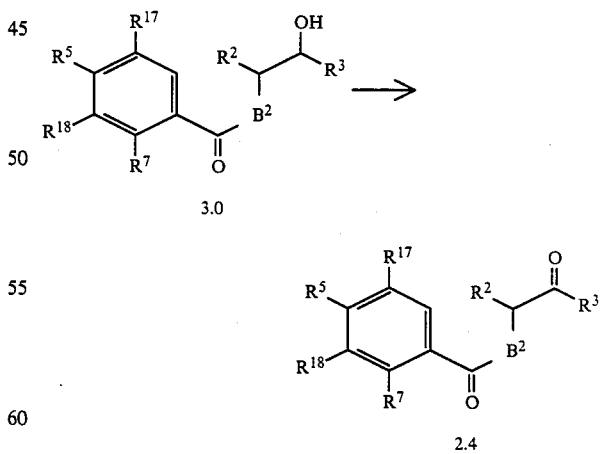

Preferred oxidizing agents are Jone's reagent, comprising a solution of chromium trioxide in acetone and water, and pyridinium chlorochromate; other oxidizing agents may also be used. When the oxidant is Jone's reagent, then the compound of formula 3.0 is dissolved in acetone; and when pyridinium chlorochromate is used, compound 3.0 is dissolved in anhydrous dichloromethane. The oxidation with Jone's reagent is carried out at a low temperature, typically −25 to +15° C., and a preferred temperature is about 0° C. The preferred temperature for use of pyridinium chlorochromate is about 25° C., although other temperatures may also be used.

(1) A compound of formula 4.0 is allowed to react with a compound of formula 5.2 and a base to produce a compound of formula 2.5:

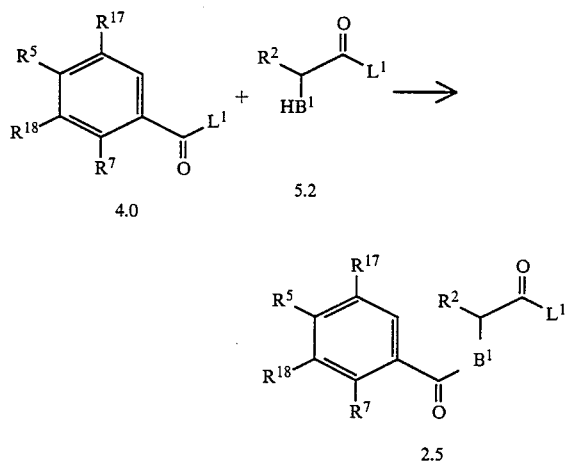

The base is typically a tertiary amine base such as pyridine, triethylamine, or diisopropylethylamine, preferably diisopropylethylamine. A suitable solvent for the reaction is chosen from among dichloromethane, chloroform, carbon tetrachloride, 1,2-dichloroethane, benzene, toluene, and the like. The reaction is preferably carried out at temperatures ranging from 0° C. to 25° C.; a wider temperature range may also be employed, e.g., −10 to +50° C.

If the compound of formula 5.2 is supplied as an acid addition salt, it is necessary to liberate compound 5.2 from the added acid. A base is needed to do so, and suitable bases are $M_2{}^+CO_3{}^{2-}$, $M^+HCO_3{}^{2-}$, and tertiary amine bases, such as pyridine, triethylamine, and diisopropylethylamine. A preferred method for liberating compound 5.2 and for carrying out the reaction yielding compound 2.4 is to combine a sufficient amount of a tertiary amine base with compounds 4.0 and 5.2.

Compounds of general formula 3.0 are prepare by process (m) below:

(m) A compound of formula 4.0 is allowed to react with a compound of formula 6.0 and with a base to produce a compound of formula 3.0:

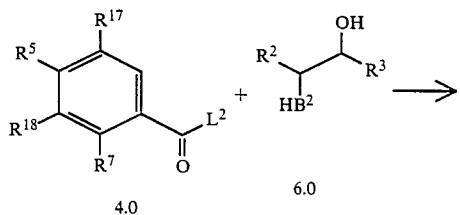

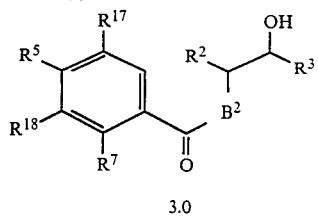

The base is typically a tertiary amine base such as pyridine, triethylamine, or diisopropylethylamine, preferably diisopropylethylamine. A suitable solvent for the reaction is chosen from among dichloromethane, chloroform, carbon tetrachloride, 1,2-dichloroethane, benzene, toluene, and the like. The reaction is preferably carried out at temperatures ranging from 0° C. to 25° C.; a wider temperature range may also be employed, e.g., −10° to +50° C.

If the compound of formula 6.0 is supplied as an acid addition salt, it is necessary to liberate compound 6.0 from the added acid. A base is needed to do so, and suitable bases are $M_2{}^+CO_3{}^{2-}$, $M^+HCO_3{}^{2-}$, as well as tertiary amine bases, such as pyridine, triethylamine, and diisopropylethylamine. A preferred method for liberating compound 6.0 and for carrying out the reaction yielding compound 3.0 is to combine a sufficient amount of a tertiary amine base with compounds 4.0 and 6.0. A sufficient amount of base is about two moles of base per mole of compound 6.0, provided that the molar ratio of compound 4.0 to 6.0 is one.

Compounds of formulas 4.0, 5.1, 5.2, and 6.0 above are commercially available or may be prepared by standard methods well known to practitioners of the art.

The compounds of the present invention can be used to treat allergies, inflammation and hyperproliferative skin disease, and a preferred use is for treating allergic chronic obstructive lung diseases. "Chronic obstructive lung disease" as used herein means disease conditions in which the passage of air into and out of the lungs is obstructed or diminished such as is the case in asthma, bronchitis and the like. As used herein, the term "hyperproliferative skin disease" means any condition a symptom of which is accelerated skin cell production, flaking, scales or papular lesions, including, for example, psoriasis, eczema, dandruff and the like.

The anti-allergy method of this invention is identified by tests that measure inhibition of leukotriene release in sensitized guinea pigs by compounds of the invention. This procedure is as follows.

Peptidoleukotriene Release Inhibition in Lung Assay

First, kill sensitized guinea pigs by a blow to the head, remove the lungs and clean them of visible connective tissue, trachea and large blood vessels. Slice the lungs from individual animals into fragments approximately 1 mm in thickness using a McIlwain tissue chopper and wash them with oxygenated Tyrode's buffer. Transfer weighed aliquots (approximately 400 mg wet weight) of lung into vials containing 2 ml of fresh Tyrode's solution (containing 10 mM cysteine) and incubate in the presence or absence of test compound for 12 minutes at 37° C., challenge the tissues with 20 μg ovalbumin/ml (final concentration) and incubate for 15 minutes. To measure leukotriene release, extract an aliquot of supernatant fluid with 4 volumes of 100% ethanol. After removal of the precipitated protein, dry the clear fluid under a stream of $N_2$ gas. Measure the leukotriene content by a radioimmunoassay using [$^3$H]LTC$_4$ (leukotriene C$_4$) and antiserum obtained from New England Nuclear. The cross-reactivity of the antiserum for LTC$_4$ is 55%. Calculate percent inhibition of leukotriene release by comparing for each lung the release in the presence of the test compound to that in the absence of test compound. Representative compounds of the invention at a relative dose of 50 μm of tissue inhibited leukotriene release in the test procedure as indicated below in Table 1.

Representative compounds of the invention at a final concentration of 50 μm inhibited leukotriene release in the test procedure as indicated below in Table 1.

mM KCl, 0.7 mM MgCl$_2$, 0.5 mM EDTA and 10 mM glucose at pH 7.4).

Preincubate MC-9 cells (0.39 ml at 7.5×10$^6$ cells/ml) without or with test compound dissolved in dimethylsulfoxide (DMSO) vehicle (to a final volume 1 μl) for 4 minutes then incubate for 5 minutes with [$^{14}$C]arachidonic acid (Amersham, 59 Ci/mole) at a 9 μM final concentration, and A23187 (Calbiochem) at a 1 μM final concentration in 10 μl of water:ethanol (9:1). Stop the reaction by addition of methanol (0.4 ml), and remove cellular debris by centrifugation. Run aliquots (250 μl) of the incubations on a Waters two-pump HPLC system fitted with a Waters radial compression column (C18, 10 micron, 8×100 mm, micro-Bondapak)

TABLE 1

| R$^1$ | R$^2$ | R$^3$ | R$^4$ | R$^5$ | R$^6$ | R$^7$ | % Inhibition of Peptidoleukotriene Release in Guinea Pig Lung |
|---|---|---|---|---|---|---|---|
| (CH$_2$)$_4$$^a$ | CH$_3$ | OAc$^b$ | | H | OAc$^b$ | H | 69 |
| (CH$_2$)$_4$$^a$ | CH$_3$ | OH | | H | OH | H | 61 |
| (CH$_2$)$_4$$^a$ | CH$_3$ | O$^-$NA$^+$ | | H | O$^-$Na$^+$ | H | 71 |
| (CH$_2$)$_4$$^a$ | CH$_3$ | OC(O)Bu—t$^c$ | | H | 5 | | |
| (CH$_2$)$_4$$^a$ | OAc | OAc$^b$ | | H | OAc | H | 39 |
| (CH$_2$)$_4$$^a$ | OH | OH | | H | OH | •H | 28 |
| (CH$_2$)$_4$$^a$ | Ph | OAc$^b$ | | H | OAc$^b$ | H | 66 |
| (CH$_2$)$_4$$^a$ | Me | H | | H | OAc$^b$ | OAc$^b$ | 62 |
| (CH$_2$)$_4$$^a$ | Me | OAc$^b$ | | OAc$^b$ | H | H | 84 |
| (CH$_2$)$_4$$^a$ | Me | H | | H | OAc$^b$ | H | 9 |
| (CH$_2$)$_4$$^a$ | Me | OCH$_3$ | | H | OCH$_3$ | H | 33 |
| CH$_3$ | (CH$_2$)$_4$$^d$ | $\underset{\underset{\text{OC—C—NH}_3\text{Cl}}{\parallel\ \ \ \|}}{\text{O  H}}$ | | H | $\underset{\underset{\text{OC—C—NH}_3\text{Cl}}{\parallel\ \ \ \|}}{\text{O  H}}$ | H | 72 |
| CH$_3$ | CH$_3$ | Ph | OAc$^b$ | H | OAc$^b$ | H | 45 |
| H | CH$_3$ | Ph | OAc$^b$ | H | OAc$^b$ | H | 12 |
| H | (CH$_2$)$_4$$^d$ | | OAC$^b$ | H | OAc$^b$ | H | 36 |
| (CH$_2$)$_3$$^a$ | Ph | | OAc$^b$ | H | OAc$^b$ | H | 76 |

$^a$Representation of R$^1$ and R$^2$ together
$^b$OAc = acetyloxy
$^c$Bu— =tertiary butyl
$^d$Representation of R$^2$ and R$^3$ together The compounds of this invention inhibit 5-lipoxygenase activity, which inhibitory activity has been associated with antiinflammatory and antihyper-proliferative activity. The compounds of the invention are thus useful for the treatment of inflammation, arthritis, bursitis, tendonitis, gout and other inflammatory conditions as well as hyperproliferative skin diseases. 5-lipoxygenase inhibition by the compounds of the invention may be demonstrated by the procedure described below.

5-Lipoxygenase Assay

Use the interleukin-3-dependent murine mast cell clone, MC-9, to test the effects of representative compounds of the invention on lipoxygenase activity. Grow the MC-9 cell line in suspension culture (0.4 to 1.2×10$^6$ cells/ml) in RPMI 1640 medium (Gibco) with 10% fetal bovine serum (Hyclone) and 2–5% concanavalin-A conditioned supernatant (Musch et. al., (1985) *Prostagandins* 29, 405–4307). Harvest the cells, wash them twice by centrifugation, and resuspend them in a Ca$^{++}$-free HEPES buffer (25 mM HEPES, 125 mM NaCl, 2.5 and C18 "Guard Pak". Initially elute the column at 3 ml/min with water:methanol:acetic acid (67:33:0.08) containing 1 mM EDTA adjusted to pH 6.0 with ammonium hydroxide (Pump A). At 4 minutes, establish a linear gradient to reach 100% methanol (Pump B) at 9 minutes. Between 13 and 14 minutes, exchange for the initial eluting solvent and by 19 minutes the column will be reequilibrated for the next sample. Analyze the effluent by a continuous flow radioactivity monitor (model ROMONA-D) interfaced with a Hewlett Packard Lab Automation System for quantitation of radioactive products. These products are predominantly leukotriene C$_4$ (LTC$_4$), which elutes at 6 minutes, and 5-hydroxyeicosatetraenoic acid (5-HETE), which elutes at 11 minutes (Musch et. al., supra). Use the results with and without test compound to calculate percent inhibition of LTC$_4$ and 5-HETE production for representative compounds of the invention as shown in Table 2 below. Doses in table 2 are 50 μM unless otherwise noted.

TABLE 2

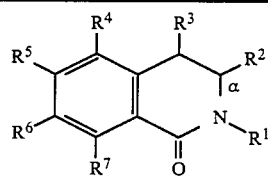

| $R^1$ | $R^2$ | $R^3$ | $R^4$ | $R^5$ | $R^6$ | $R^7$ | α Double Bond | % Inhibition 5-HETE | LTC$_4$ |
|---|---|---|---|---|---|---|---|---|---|
| (CH$_2$)$_4$[a] | CH$_3$ | | OAc[b] | H | OAc[b] | H | yes | 99 | 98 |
| | | | | | | | | 93[d] | 90[d] |
| | | | | | | | | 62[e] | 54[e] |
| | | | | | | | | 65[f] | 59[f] |
| | | | | | | | | 50[g] | 57[g] |
| (CH$_2$)$_3$[a] | | Ph | OAc[b] | H | OAc[b] | H | yes | 18 | 10 |
| (CH$_2$)$_4$[a] | Ph,OH | | OH | H | OH | H | no | 23 | — |
| (CH$_2$)$_4$[a] | CH$_3$,OH | | H | H | OAc[b] | H | no | 5 | — |
| (CH$_2$)$_4$[a] | | Ph | OAc[b] | H | OAc[b] | H | yes | 21 | — |
| (CH$_2$)$_4$[a] | | OH | OH | H | OH | H | yes | 18 | — |
| (CH$_2$)$_4$[a] | | OAc | OAc[b] | H | OAc[b] | H | yes | 2 | — |
| (CH$_2$)$_4$[a] | | CH$_3$ | OCOCH$_2$NH$_3$Cl | H | OCOCH$_2$NH$_3$Cl | H | yes | 99 | — |
| (CH$_2$)$_4$[a] | | CH$_3$ | OCOBu—t | H | OCOBu—t | H | yes | 45 | — |
| (CH$_2$)$_4$[a] | | CH$_3$ | H | H | OAc[b] | OAc[b] | yes | 98 | — |
| (CH$_2$)$_4$[a] | | CH$_3$ | O$^-$Na$^+$ | H | O$^-$Na$^+$ | H | yes | 88 | — |
| (CH$_2$)$_4$[a] | | CH$_3$ | OH | H | OH | H | yes | 100 | — |
| (CH$_2$)$_4$[a] | | CH$_3$ | H | H | Oac[b] | H | yes | 19 | — |
| (CH$_2$)$_4$[a] | | CH$_3$ | OAc[b] | OAc[b] | H | H | yes | 74 | — |
| (CH$_2$)$_4$[a] | | CH$_3$ | OAc[b] | H | OAc[b] | H | yes | 46 | 5 |
| (CH$_2$)$_4$[a] | | CH$_3$ | OCH$_3$ | H | OCH$_3$ | H | yes | 8 | — |
| H | H | CH$_3$ | OAc[b] | H | OAc[b] | H | yes | 43 | 40 |
| H | H | Ph | OAc[b] | H | OAc[b] | H | yes | 19 | 16 |
| H | H | Ph | OH | H | OH | H | yes | 17 | 16 |
| H | CH$_3$ | Ph | OAc[b] | H | OAc[b] | H | yes | 31 | 27 |
| CH$_3$ | CH$_3$ | Ph | OAc[b] | H | OAc[b] | H | yes | 5 | — |
| H | (CH$_2$)$_3$[c] | | OH | H | OH | H | yes | 31 | — |
| H | (CH$_3$)$_4$[c] | | OH | H | OH | H | yes | 31 | — |
| H | (CH$_3$)$_4$[c] | | OAc[b] | H | OAc[b] | H | yes | 56 | — |
| CH$_3$ | (CH$_2$)$_3$[c] | | OAc[b] | H | OAc[b] | H | yes | 56 | — |
| H | (CH$_2$)$_4$[c] | | OAc[b] | H | OAc[b] | H | yes | 56 | 41 |
| (CH$_2$)$_4$[a] | Ph,OH | | OH | H | OH | H | no | 23 | 32 |

[a] Representation of $R^1$ and $R^2$ together
[b] OAc = acetyloxy
[c] Representation of $R^2$ and $R^3$ together
[d] 25 μM dose
[e] 12.5 μM dose
[f] 6.25 μM dose
[g] 3.12 μM dose The antiinflamatory activity Of the compounds can be demonstrated by standard test procedures, such as the reverse passive Arthus reaction (RPAR) as descried below or as described in Myers et al., Inflammation 9(1):91-98 (1985).

Reversed Passive Arthus Reaction (RPAR) Assay

Male Lewis inbred albino rats weighing 180-220 grams obtained from Charles River Breeding Laboratories are used in these experiments. House the rats 3 animals/cage and allow food and water ad libitum. Number the animals 1 to 3 in each cage and color mark them for identification purposes.

Prepare all reagents and drugs just prior to the study. Without shaking, solubilize crystallized and lyophilized bovine serum albumin (BSA), obtained from Sigma Chemical Company, in cold sterile pyrogen-free saline (10 mg/ml PFS). Suspend lyophilized anti-bovine serum albumin (IgG Fraction), obtained from Cappel Laboratories, in sterile distilled water and dilute with cold pyrogen-free saline (PFS) just prior to use. The final concentration of anti-bovine serum albumin will be 0.5 mg/ml of PFS. Both BSA and anti-BSA solutions should be iced during use. Suspend or solubilize drugs in an aqueous solution of methyl cellulose (MC) with a homogenizer just prior to administration.

Dose groups of animals (6/group) with drug in methyl cellulose (MC) by gastric lavage one hour prior to sensitization with BSA. Give controls MC alone and include drug-standard in each assay for verification purposes. Prepare drugs so as to provide a dose for a 200 gram animal which is equivalent to the mg/kg dose for the experiment. Thus each rat receives an oral dose in a volume of approximately 2.0 ml. Lightly anesthetize the animals with ether one hour after dosing and sensitize by injecting into the penile vein about 0.2 ml of PFS containing 1.0 mg of BSA. One hour later inject them in the plantar region of one hind paw with 0.1 ml of pyrogen free saline (PFS) containing 1.0 mg of BSA. One hour later inject them in the plantar region of one hind paw with 0.1 ml of PFS containing 0.1 mg of the anti-bovine serum albumin. Immediately after the subplantar injection, dip the injected paw (up to the lateral maleolus) into the mercury well of a plethysmograph. Convert the volume of mercury displaced to weight and record. Consider this value to be the control paw volume for the animal. Also record paw volumes with a plethysmograph during the development of the inflammation at 2 and 4 hours post-challenge.

Compound E (8,10-bis(methoxy)-1,2,3,4-tetrahydro-11-methyl-6H-benzo[b]quinolizin-6-one) demonstrated a 59% inhibition of paw swelling in the above procedure when a dose of 50 mg/kg was administered p.o.

In the preferred anti-allergy, antiinflammatory or anti-hyperproliferative skin disease use, the compounds of this invention are used to treat patients by administering an anti-allergy, antiinflammatory or antihyperproliferative skin disease effective amount thereof.

The active compounds can be administered orally, topically, parenterally, or by oral or nasal inhalation. The preferred mode of administration is orally or intravenously.

Formulations for topical application, e.g., for use in treating hyperproliferative skin diseases, may include the liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. For example, such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Lotions may be formulations with an aqueous or oily base and will, in general, also include one or more of stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e. sterile solutions or suspensions are also made by conventional means. Inhalation administration can be in the form of a nasal or oral spray. Insufflation is also contemplated.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may comprise from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

Liquid form preparations include solutions, suspensions and emulsions. As an example may be mentioned water or water-propylene glycol solutions for parenteral injection.

Liquid form preparation may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Preferably, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration will be regulated according to the judgement of the attending clinician considering such factors as age, condition and size of the patient as well as severity of the disease being treated.

A typical recommended dosage regimen for treating inflammation is oral administration of from 0.5 to 50 mg/kg/day preferably 2 to 40 mg/kg/day, in two to four divided doses to achieve relief of the symptoms. Alternatively, intravenous administration of 0.1 to 10 mg/kg/day is recommended, preferably 0.6 to 8 mg/kg/day in two to four divided doses to achieve relief of the inflammation symptoms.

The compounds are effective non-adrenergic, non-anticholinergic antianaphylactic agents. The compounds may be administered by any conventional mode of administration for treatment of allergic reactions employing an effective amount of a compound of formula 1.0 for such mode. For example, when administered orally they may be administered at doses from about 0.2 to 10 mg/kg of body weight; when administered parenterally, e.g., intravenously, the compounds may be administered at dosages of from about 0.1 to 5 mg/kg body weight; when administered by inhalation (aerosol or nebulizer) the compounds may be administered at dosages of about 0.1 to 10 mg per puff, one to four puffs may be taken every 4 hours.

In a preferred method of treating hyperproliferative skin diseases, a pharmaceutical formulation comprising a compound of formula 1.0, (usually in concentrations in the range of from about 0.001 percent to about 10 percent, preferably from about 0.1 percent to about 5 percent) together with a non-toxic, pharmaceutically acceptable topical carrier, is applied several times daily to the affected skin until the condition has improved. Topical applications may then be continued at less frequent intervals (e.g. once a day) to control mitosis in order to prevent return of severe disease conditions.

The following examples illustrate specific embodiments of the present invention including preparation of compounds, intermediates and starting materials.

EXAMPLE ONE

Dissolve 2-acetyl-1-[3,5-bis(acetyloxy)benzoyl]-piperidine (510 mg) in methanol (5 ml), and add potassium carbonate (406 mg). Keep the reaction mixture under a nitrogen atmosphere, and stir it at 25° C. for 17 hours. Dilute the reaction mixture with water (25 ml), and acidify it to pH =2 with 1N hydrochloric acid. Extract the resulting mixture of solid and liquid with chloroform, and wash the combined extracts with water. Separate the layers, combine all aqueous solutions, which contain a suspended precipitate, and collect the precipitate on a filter. Wash the precipitate with water and dry it to give 1,2,3,4-tetrahydro-8,10-dihydroxy-11-6H-benzo[b]quinolizin-6-one, m.p. 319°-321° C. (from ethanol(EtOH)).

By using essentially the same procedure, the following compounds may be prepared:

1,2,3,4-tetrahydro-8,10,11-trihydroxy-6H-benzo[b]quinolizin-6-one, m.p. 259-263° C. (from ethyl acetate (EtOAc));

5,7-dihydroxy-4-phenyl-1(2H)-dihydroisoquinolinone, m.p. 335°-340° C. (d.) (from methanol (MeOH));

1,2,3,4-tetrahydro-9,10-dihydroxy-11-methyl-6H-benzo[b]quinolizin-6-one, m.p. 190°-193° C. (from acetone petroleum ether (Me$_2$-CO pet. eth.));

1,3,4,5-tetrahydro-8,10-dihydroxy-phenanthridin-6(2H)-one, m.p. >300° C. (from dilute aqueous hydrochloric acid);

1,2,3,4,11,11a-hexahydro-8,10,11-trihydroxy-11-phenyl-6H-benzo[b]quinolizin-6-one, m.p. 300°-303° (from chloroform (CHC13)); and 2,3-dihydro-7,9-dihydroxy-10-phenylpyrrolo[1,2-b]isoquinolin-5(1H)-one, m.p. 220°-222° C. (from EtOAc).

EXAMPLE TWO

Reflux crude 8,10-bis(acetyloxy)-1,2,3,4-tetrahydro-11-methyl-6H-benzo[b]quinolizin-6-one (11.8 g), acetic anhydride (20.2 ml), pyridine (20.2 ml), and chloroform (400 ml) for 20 hrs. Concentrate the cooled solution to dryness, and dilute the residue with ethyl acetate. Separate the resulting crystals by filtration, and concentrate the mother liquor. Chromatograph the residue over silica gel, and elute the column with 10% ethyl acetate in dichloromethane. Combine and concentrate fractions, and crystallize to obtain 9,10-bis(acetyloxy)-1,2,3,4,11,11a-hexahydro-11-methylene-6H-benzo[b]quinolizin-6-one, m.p. 129°-132° C. (from CHCl$_3$-EtOAc).

By using essentially the same procedure, the following compounds may also be made:

8,10-bis(acetyloxy)-1,2,3,4,-tetrahydro-11-phenyl-6H-benzo[b]quinolizin-6-one, m.p. 179°-182° C. (from CHCl$_3$-pet. eth.);

8,10,11-tris(acetyloxy)-1,2,3,4-tetrahydro-6H-benzo[b]quinolizin-6-one, m.p. 186°-187° C. (from 2-propyl ether-dichloromethane (2-Pr$_2$OCH$_2$Cl$_2$));

8,10-bis(2,2-dimethyl-1-oxopropoxy)-11-methyl-1,3,4,6-tetrahydro-6H-benzo[b]quinolizin-6-one, m.p. 126°-129° C. (from CHCl$_3$-pet. eth.);

7,8-bis(acetyloxy)-1,2,3,4-tetrahydro-11-methyl-6H-benzo[b]quinolizin-6-one, m.p. 181°-182° C. (from acetic anhydride-pyridine);

8-acetyloxy-1,2,3,4-tetrahydro-11-methyl-6H-benzo[b]quinolizin-6-one, m.p. 116.5°-117.5° C. (from Me$_2$CO);

9,10-bis(acetyloxy)-1,2,3,4-tetrahydro-11-methyl-6H-benzo[b]quinolizin-6-one, m.p. 186.5°-188.5° C. (from Me$_2$CO-pet. eth.); 7,9-bis(acetyloxy)-2,3-dihydro-10-methyl-pyrrolo[1,2b]isoquinolin-5(1H)-one, m.p. 180°-182° C. (from CHCl$_3$-pet. eth.);

5,7-bis(acetyloxy)-4-methyl-1(2H)-isoquinolinone, m.p. 226°-228° C. (from CH$_2$Cl$_2$ carbon tetrachloride (CCl$_4$));

5,7-bis(acetyloxy)-4-phenyl-1(2H)-isoquinolinone, m.p. 248°-251° C. (from EtOAc);

5,7-bis(acetyloxy)-3-methyl-4-phenyl-1(2H)-isoquinolinone, m.p. 294°-296° C. (from CHCl$_3$);

5,7-bis(acetyloxy)-2,3-dimethyl-4-phenyl-1(2H)-isoquinolinone, m.p. 182°-185° C. (from Me$_2$CO-pet. eth.);

8,10-bis(acetyloxy)-1,3,4,5,6-tetrahydro-6(2H)-phenanthridinone, m.p. 257°-259.5° C. (from MeOH Me$_2$CO);

8,10-bis(acetyloxy)-1,2,3,4-tetrahydro-11-methyl-6H-benzo[b]quinolizin-6-one , m.p. 174.0°-176.0° C. (from 2-Pr$_2$O-Me$_2$CO);

7,9-bis(acetyloxy)-2,3-dihydro-10-phenyl-6H-pyrrolo[1,2-b]isoquinolin-5(1H)-one, m.p. 184°-185° C. (from CH$_2$Cl$_2$-pet. eth.);

8-acetyloxy-1,2,3,4,11,11a-hexahydro-11-hydroxy-11-methyl-6H-benzo[b]quinolizin-6-one, m.p. 167°-169° C. (from Me$_2$CO).

EXAMPLE THREE

Dissolve 1,2,3,4-tetrahydro-8,10-dihydroxy-11-methyl-6H-benzo[b]quinolizin-6-one (1.36 g) in 0.2N sodium hydroxide solution (55.45 ml) in a nitrogen atmosphere, and then treat the solution with decolorizing carbon. Filter the mixture through diatomaceous earth and lyophilize the filtrate to obtain 1,2,3,4-tetrahydro-8,10-dihydroxy-11-methyl-6H-benzo[b]quinolizin-6-one, disodium salt, as a red solid.

EXAMPLE FOUR

Combine N-(tert.-butyloxycarbonyl)-glycine (8.8 g), 1,1'-carbonyldiimidazole (8.1 g), and N,N-dimethylformamide (40 ml) at 10° C., and, after 10 min., add 8,10-bis(acetyloxy)-1,2,3,4-tetrahydro-11-methyl-6H-benzo[b]quinolizin-6-one (2.45 g) in N,N-dimethylformamide (40 ml) followed by 4-dimethylaminopyridine (6.1 g). Stir the reaction mixture at 25° C. overnight. Dilute the reaction mixture with water (250 ml) and extract with ethyl acetate. Combine the organic extracts, and wash them sequentially with water, saturated sodium bicarbonate solution, water, 5% aqueous acetic acid, and with water. Concentrate the dried, filtered ethyl acetate solution to give a residue. Chromatograph the residue over silica gel, and elute the column with 1°–2% methanol in dichloromethane. Combine fractions to give 8,10bis[(aminoacetyl)oxy]-11-methyl-1,2,3,4-tetrahydro-6H-benzo[b]quinolizine-6-one, m.p. 163°–164° C. (from MeOH-CH$_2$Cl$_2$). Use this material directly in the next step.

Dissolve 8,10-bis[(aminoacetyl)oxy]-11-methyl-1,2,3,4-tetrahydro-6H-benzo[b]quinolizine-6-one (0.92 g) in dry dichloromethane (100 ml), and pass a stream of hydrogen chloride gas through the solution for 45 min. at ambient temperature (about 25° C.). Stir the resulting mixture at 25° C. for 2 hours, and filter to collect the precipitated crystals. Wash the collected crystals with ether and acetone, and dry and crystallize them to obtain 8,10-bis[(aminoacetyl)oxy]-11-methyl-1,2,3,4-tetrahydro-6H-benzo[b]quinolizine-6-one dihydrochloride, m.p. 202°–205° C. (from MeOH-ether, as a hemihydrate).

EXAMPLE FIVE

Add 5,7-bis(acetyloxy)-3-methyl-4-phenyl-1(2H)-isoquinolin-1-one (2.91 g) dissolved in N,N-dimethylformamide (170 ml) to a mixture of sodium hydride (0.35 g of a 60% mineral oil dispersion) and N,N-dimethylformamide (25 ml). Stir the mixture at 25° C. for 1 hour, and then add methyl iodide (6.72 g). Stir the resulting mixture overnight, and pour it cautiously onto ice (600 g) and ether (250 ml). Collect the precipitated crystals by filtration, then dry and crystallize them to obtain 57-bis(acetyloxy)-2,3-dimethyl-4-phenyl-1(2H)-isoquinolin-1-one, m.p. 182°–185° C. (from Me$_2$CO-pet. eth.).

By using essentially the same procedure, the following compound may also be prepared:
8,10-bis(acetyloxy)-1,3,4,5-tetrahydro-5-methyl-6(2H)-phenanthridinone, m.p. 165°–167.5° C. (from CH$_2$Cl$_2$-pet. eth.).

EXAMPLE SIX

Reflux a solution of 2-acetyl-1-[3,5-bis(methoxy)benzoyl]piperidine (4.62 g), trifluoroacetic acid (3 ml), and carbon tetrachloride (97 ml) for 20 hours under nitrogen. Cool the solution to 25° C., and sequentially wash it with water, 1M sodium bicarbonate solution, and with water. Concentrate the dried, filtered organic solution, and cool it to induce crystallization. Recrystallize the resulting solid to obtain 8,10-bis(methoxy)-1,2,3,4-tetrahydro-11-methyl-6H-benzo[b]quinolizin-6-one, m.p. 165°–168° C. (from EtOAc).

EXAMPLE SEVEN

Shake a 25° C. mixture of 1,2,3,4-tetrahydro-8,10,11-trihydroxy-6H-benzo[b]quinolizin-6-one (2.00 g), rodium-on-aluminum oxide (1.10 g), and tert.-butanol (220 ml) containing acetic acid (1 ml) under a hydrogen pressure of 60 psi. For continuous shaking of the pressurized mixture, use a Paar apparatus; and for complete reaction, shake the mixture for at least 72 hrs. Then open the vessel and filter the mixture, washing the collected catalyst with tert.-butanol. Combine and concentrate the filtrates, and partition the residue between ethyl acetate and IM sodium bicarbonate solution. Sequentially wash the separated organic layer with 0.1N hydrochloric acid solution, with water, and with brine. Filter the dried solution and concentrate it to obtain 1,2,3,4-tetrahydro-8,10-dihydroxy-6H-benzo[b]quinolizin-6-one, m.p.214°–215° C. (from EtOAc).

PREPARATIVE EXAMPLE ONE

Stir a mixture of 3,5-bis(acetyloxy)benzoyl chloride (25.7 g), 2-(1,1-dimethoxyethyl)piperidine hydrochloride (21.1 g), diisopropylethylamine (28 g), and dichloromethane (400 ml) at 0°–5° C. for 1.75 hours, and stir the mixture at 25° C. overnight. Wash the solution sequentially with water, 1M sodium bicarbonate solution, and brine. Filter and concentrate the dried organic solution to give an oil; and use the oil directly in the next step.

Disolve the foregoing oil in ether (150 ml), cool the ethereal solution, and pour it into cooled (0°–5° C.) 1N hydrochloric acid solution (100 ml). Stir the mixture for 1 hour, separate the layers, and wash the ethereal layer first with 1M sodium bicarbonate solution and then with water. Concentrate the filtered, dried organic solution to obtain 2-acetyl-1-[3,5-bis(acetyloxy)benzoyl]piperidine as an oil, $v_{max}$ 1780, 1730, and 1640 cm$^{-1}$.

By using essentially the same procedure, the following intermediate compounds may also be prepared:
ethyl 1-[3,5-bis(acetyloxy)benzoyl]-2-piperidinecarboxylate, as an oil;
2-acetyl-1-[3,5-bis(acetyloxy)benzoyl]piperidine, m.p. 125.5°–127.0° C. (from ether (Et$_2$O)-CH$_2$Cl$_2$);
1-[3,5-bis(acetyloxy)benzoyl]-α-methyl-2-pyrrolidinemethanol, m.p. 148°–151° C. (from CH$_2$Cl$_2$-pet. eth.);
3,5-bis(acetyloxy)-N-(2-hydroxypropyl)benzamide, as an oil;
1-[3,5-bis(acetyloxy)benzoyl]-α-phenyl-2-piperidinemethanol, m.p. 171°–172° C. (from Et$_2$O);
1-[3,5-bis(methoxy)benzoyl]-α-methyl-2-piperidinemethanol, as an oil;
3,5-bis(acetyloxy)-N-(2-hydroxy-1-methyl-2-phenylethyl)benzamide, m.p. 74°–75° C. (from CCl$_4$);
3,5-bis(acetyloxy)-N-(2-hydroxycyclohexyl)benzamide, m.p. 174°–175° C. (from pet. eth.-CH$_2$Cl$_2$);
3,5-bis(acetyloxy)-N-(2-oxo-2-phenylethyl)benzamide, m.p. 160°–161.5° C. (from EtOAc); and
2-acetyl-[3,4-bis(acetyloxy)benzoyl]piperidine, as an oil eluted from silica gel by 10% EtOAc-CHCl$_3$.

PREPARATIVE EXAMPLE TWO

Add pyridinium chlorochromate (2.96 g) and 3Å, 1/16-inch molecular sieves (2.96 g) to a solution of 1-[3,5-bis(acetyloxy)benzoyl]-α-phenyl-2-piperidinemethanol (2.66 g) in dry dichloromethane (60 ml). Stir the resulting mixture at 23° C. for 4 hours. Filter the mixture through diatomaceous earth, and concentrate the filtrate. Chromatograph the residue over silica gel, and elute the column with 10% ethyl acetate in chloroform. Combine appropriate fractions, concentrate them, and crystallize the residue to obtain 2-benzoyl-1-[3,5-bis(acetyloxy)benzoyl]-piperidine, m.p. 77°–79° C. (from ether-pet. eth.).

By using essentially the same procedure, the following intermediate compounds may also be made:
2-acetyl-1-[3,5-bis(acetyloxybenzoyl)pyrrolidine, as an oil;
3,5-bis(acetyloxy)-N-(1-methyl-2-oxopropyl)benzamide, eluted from silica gel by 10% ethyl acetate-chloroform, m.p. 113°–115° C. (from EtOH);
3,5-bis(acetyloxy)-N-(2-oxocyclohexyl)benzamide, eluted from silica gel by 5% EtOAc in CHCl$_3$, m.p. 144°–146° C. (from Et$_2$O); and
3,5-bis(acetyloxy)-N-(1-methyl-2-oxo-2-phenylpropyl)-benzamide, as an oil eluted from silica gel by CHCl$_3$.

PREPARATIVE EXAMPLE THREE

Add Jone's reagent (26.9 ml) dropwise to 1-[3,5-bis(-methoxy)benzoyl]-α-methyl-2-piperidinemethanol (15.9 g) dissolved in acetone (188 ml) at 0° C. To destroy excess oxidant, add 2-propanol (5 ml) 5 min. after completion of the addition, and allow the reaction mixture to stand for 30 min. Dilute the mixture with brine (200 ml), and separate the layers. Extract the aqueous layer with ether, and combine the organic solutions. Wash them sequentially with water, 1N sodium bicarbonate, water, and brine. Concentrate the dried, filtered organic solution, and chromatograph the residue over silica gel. Elute the column with 10% ethyl acetate in cloroform, and combine and concentrate the fractions to obtain 2-acetyl-1-[3,5-(bis)methoxybenzoyl]piperidine, as an oil.

*J. Chem. Soc.* (1953, 2548) teaches how to make Jone's reagent, which comprises a solution of chromium trioxide in a mixture of water and acetone.

By using essentially the same method, the following compound may also be prepared:

2-acetyl-1-[3,5-(bis)methoxy]-piperidine, eluted from silica gel by 10% EtOAc-CHCl$_3$, as an oil.

PREPARATIVE EXAMPLE FOUR

By applying the method taught by *J. Am. Chem. Soc.* (1955, 77, 3823), the following benzoyl chlorides may be prepared from the corresponding benzoic acids:

2,3-diacetoxybenzoyl chloride, as a yellow solid (from toluene cyclohexane); and 3,5-dimethoxybenzoyl chloride, b.p. 138°–142° C. at 10 mm of Hg.

PREPARATIVE EXAMPLE FIVE

By applying the method taught by *J. Am. Chem. Soc.* (1955, 77, 3823), the following acetoxylated benzoic acids may be prepared from the corresponding, commercially available, hydroxylated benzoic acids:

3-acetoxybenzoic acid, m.p. 90°–92° C. (from CHCl$_3$-pet. eth.);

2,3-diacetoxybenzoic acid, m.p. 156.5°–159.5° C. (from EtOAc).

KNOWN INTERMEDIATE COMPOUNDS

To make compounds of the present invention, certain intermediate compounds are needed. These latter compounds may be prepared according to standard, published methods known to those versed in the art. The following list provides the names of needed intermediate compounds as well as references disclosing methods for making the intermediates.

3,4-diacetoxybenzoyl chloride: *J. Chem. Soc.* 1928 2908;

3-acetoxybenzoyl chloride: *Liebigs Annalen der Chemie* 1925, 442, 42;

3,5-diacetoxybenzoic acid: *J. Am. Chem. Soc.* 1955, 77, 3823;

3,4-diacetoxybenzoic acid: *Chem. Ber.* 1926, 59, 234;

2-(1,1-dimethoxyethyl)-piperidine hydrochloride: *Tetrahedron*, 1981, 37, 3615;

α-phenyl-2-pyrrolidinemethanol and α-methyl-2-pyrrolidinemethanol: *Chem. Ber.* 1975, 110 1852; 1975, 108, 1293;

α-phenyl-2-piperidinemethanol: *J. Am. Chem. Soc.* 1930, 52, 4006;

ethyl dl-pipecolinate: U.S. Pat. No. 3,300,504; and 2-(1-hydroxyethyl)-piperidine: *J. Chem. Soc.* 1949, 2095.

Commercially Available Starting Materials

The Aldrich Chemical Co. provides the starting materials needed to prepare compounds of the invention via the foregoing intermediate compounds. Needed starting materials are dl-1-amino-2-propanol, dl-norephedrine hydrochloride, dl-pipecolinic acid, α-aminoacetophenone, dl-2-amino-1-cyclohexanol, 2-benzoylpyridine, N-nitrosopyrrolidine, 2-acetylpyridine, 3,5-dihydroxybenzoic acid, 2,3-dihydroxybenzoic acid, 3,4-dihydroxybenzoic acid, 3-hydroxybenzoic acid, and 3,5dimethoxybenzoic acid.

The following examples illustrate the preparation of tablets and capsules using as the active compound any of the compounds of formula 1.0, e.g. 1,2,3,4-tetrahydro-9,10-dihydroxy-11-methyl-6H-benzo[b]quinolizin-6-one.

Pharmaceutical Dosage Form Examples

Example A

| No. | Ingredient | mg/tablet | mg/tablet |
|---|---|---|---|
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix item nos. 1 and 2 in a suitable mixer for 10–15 minutes. Granulate the mixture with item no. 3. Mill the damp granules through a coarse screen (e.g., ¼") if needed. Dry the damp granules. Screen the dried granules if needed and mix with item no. 4 and mix for 10–15 minutes. Add item no. 5 and mix for 1°–3 minutes. Compress the mixture to appropriate size and weight on a suitable tablet machine.

Example B

| Capsules | | | |
|---|---|---|---|
| No. | Ingredient | mg/capsule | mg/capsule |
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
|  | Total | 250 | 700 |

Method of Manufacture

Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

I claim:

1. A compound represented by the formula

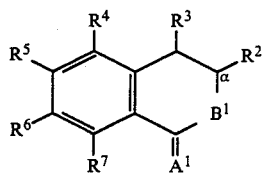

or a pharmaceutically acceptable salt or solvate thereof, wherein:

the dotted lines represent optical double bonds, one of which may present in any given compound and when both are absent, the results are single bonds terminating at the ? carbon and at the two substituents being represented by $R^3$ as defined below;

$A^1$=O or S; $B^1$ is $NR^1$ where $NR^1$ and $R^2$ together form $(CH_2)_aN$ wherein "a" is 3, 4, 5 or 6 and; $R^3$ is selected from H, alkyl, arylmethyl, aryl, OH, —O-alkyl, —O-acyl, —O-aroyl, when the dotted line terminating at $R^3$ is absent and the double bond terminating at the α carbon is present; or $R^3$ represents $CHR^0$ when $R^0$ is selected from H, alkyl, arylmethyl when the dotted line terminating at the α carbon is absent and the dotted line terminating at $R^3$ is present and represents a double bond; or $R^3$ represents two substituents selected from OH and aryl, OH and alkyl, or OH and arylmethyl when both dotted lines terminating at $R^3$ and at the α carbon are absent; $R^4$ and $R^6$ may be the same or different and each independently selected from H, halo, —$CF_3$, —$NO_2$, —$OR^8$, —acyl, —O-aroyl, -$SR^8$, —S-acyl, —S-aroyl, —$SO_2$-alkyl, —$SO_2$-aryl, —$SO_2$-aralkyl, —$N(R^8)_2$, —$N(R^8)$-acyl, —$N(R^8)$-aroyl, —$CO_2R^8$, —$C(O)N(R^8)_2$, —$CO_2$-alkyl, —$CO_2$-aryl or —$CO_2$-aralkyl, with the proviso that at least one of $R^4$ and $R^6$ is selected from —SH, —OH, —$NHR^8$, —NH-acyl, —NH-aroyl, —O-acyl, —O-aroyl, —S-acyl, or —S-aroyl; $R^5$ and $R^7$ may be the same or different and each is independently selected from H, halo, —$CF_3$, —$NO_2$, alkyl, aryl, arylmethyl, —$S(O)_c$-alkyl or —$S(O)_c$-aryl (in both of which c is 0, 1 or 2), —$OR^8$-acyl, —O-aroyl, —$SR^8$, —S-acyl, —S-aroyl, —$N(R^8)_2$, —$N(R^8)$-acyl, —$N(R^8)$-aroyl, —$CO_2R^8$ or —$C(O)N(R^8)_2$; and each $R^8$ is independently selected from H or alkyl with the proviso that $R^3$ represents arylmethyl or aryl only when at least one of $R^4$, $R^5$, $R^6$ and $R^7$ represents —O-acyl.

2. A compound of claim 1 wherein:
$A^1$ is selected from O or S;
$R^1$ together with $R^2$, represents $(CH_2)_a$, in which a is 3 or 4 so as to form a heterocyclic ring of atoms, wherein adjacent to said ring the dotted line terminating at the α carbon is present and represents a double bond;
$R^2$ also represents H or alkyl;
$R^3$ is alkyl;
$R^4$ and $R^6$ may be the same or different and each is independently selected from H, —$OR^8$, —OC(O)$R^8$, $O^-Na^+$, —$N(R^8)$-acyl, or -$N(R^8)$-aroyl with the proviso that at least one of $R^4$ and $R^6$ is selected from OH, —OC(O)$R^8$, —NH-acyl, or —NH-aroyl;
$R^5$ and $R^7$ may be the same or different and each is independently selected from H, OH, —O-acyl, or alkyl; and the dotted line terminating at the α carbon always represents a double bond.

3. A compound of claim 2 wherein $A^1$ is O and $B^1$ is $NR^1$.

4. A compound of claim 3 wherein $R^4$ and $R^6$ may be the same different and each is independently selected from H, —OC(O)$R^8$, OH, $O^-Na^+$, or —$OCH_3$ with the proviso that at least one of $R^4$ and $R^6$ is selected from OH, or —OC(O)$R^8$.

5. A compound of claim 3 wherein $R^1$ and $R^2$ together represent $(CH_2)_4$ so as to represent a carbocyclic ring.

6. A compound of claim 3 wherein $R^5$ and $R^7$ may be the same or different and each is independently selected from H, OH, or —O-acyl.

7. A compound of claim 3 wherein:
$R^1$ and $R^2$ together represent $(CH_2)_4$ so as to represent a heterocyclic ring and $R^3$ represents alkyl;
$R^4$ and $R^6$ may be the same or different and each is independently selected from H, OC(O)$R^8$, OH, $O^-Na^+$, or —$OCH_3$, with the proviso that at least one of $R^4$ and $R^6$ is selected from OH, or —OC(O)$R^8$;
$R^5$ and $R^7$ may be the same or different and each is independently selected from H, OH, or —O-acyl.

8. A compound of claim 7 wherein $R^4$ and $R^6$ may be the same or different and each is independently selected from H, —OC(O)$CH_3$, OH, $O^-Na^+$, or —$OCH_3$, with the proviso that at least one of $R^4$ and $R^6$ is selected from OH, or —OC(O)$CH_3$.

9. A compound of claim 7 wherein $R^5$ and $R^7$ may be the same or different and each is independently selected from H, OH, or —O-acyl.

10. A compound of claim 8 wherein $R^5$ and $R^7$ may be the same or different and each is independently selected from H, OH, or —O-acyl.

11. A compound of claim 10 wherein $R^5$ and $R^7$ may be the same or different and each is independently selected from H or —OC(O)$CH_3$.

12. A compound of claim 1 having the name:
1,2,3,4-tetrahydro-8,10-dihydroxy-11-6H-benzo[b]quinolizin-6-one,
1,2,3,4-tetrahydro-8,10,11-trihydroxy-6H-benzo[b]quinolizin-6-one,
1,2,3,4-tetrahydro-9,10-dihydroxy-11-methyl-6H-benzo[b]quinolizin-6-one,
2,3-dihydro-7,9-dihydroxy-10-phenylpyrrolo[1,2-b]isoquinolin-5(1H)-one,
9,10-bis(acetyloxy)-1,2,3,4,11,11a-hexahydro-11-methylene-6H-benzo[b]quinolizin-6-one,
8,10-bis(acetyloxy)-1,2,3,4,-tetrahydro-11phenyl-6H-benzo[b]quinolizin-6-one,
8,10,11-tris(acetyloxy)-2,3,4-tetrahydro-6H-benzo[b]quinolizin-6-one,
8,10-bis (2,2-dimethyl-1-oxopropoxy)-11-methyl-1,3,4,6-tetrahydro-6H-benzo[b]quinolizin-6one,
7,8-bis(acetyloxy)-1,2,3,4-tetrahydro-11-methyl-6H-benzo[b]quinolizin-6-one
8-acetyloxy-1,2,3,4-tetrahydro-11-methyl-6H-benzo[b]quinolizin-6-one,
9,10-bis(acetyloxy)-1,2,3,4-tetrahydro-11-methyl-6H-benzo[b]quinolizin-6-one,
7,9-bis(acetyloxy)-2,3-dihydro-10-methyl-pyrrolo[1,2-b]isoquinolin-5-(1H)-one,
8,10-bis(acetyloxy)-1,2,3,4-tetrahydro-11-methyl-6H-benzo[b]quinolizin-6-one,
7,9-bis(acetyloxy)-2,3-dihydro-10-phenyl-6H-pyrrolo[1,2-b]isoquinolin-5(1H)-one, 8-acetyloxy-1,2,3,4,11,11a-hexahydro-11-hydroxy-11-methyl-6H-benzo[b]quinolizin-6-one, 1,2,3,4-tetrahydro-8,10-dihydroxy-11-methyl-6H-benzo[b]quinolizin-6-one, disodium salt 8,10-bis[(aminoacetyl)oxy]-11-methyl-1,2,3,4-tetrahydro-6H-benzo[b]quinolizine-6-one, 8,10-bis[(aminoacetyl)oxy]-11-methyl-1,2,3,4-tetrahydro-6H-benzo[b]quinolizine-6-one dihydrochloride, 8,10-bis(methoxy)-1,2,3,4-tetrahydro-11-methyl-6H-benzo[b]quinolizin-6-one, or 1,2,3,4-tetrahydro-8,10-dihydroxy-6H-benzo[b]quinolizin-6-one.

13. A compound selected from

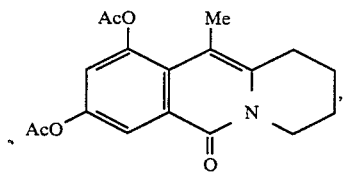,

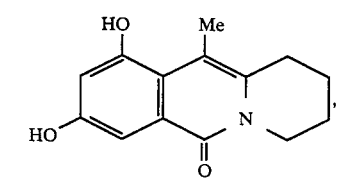,

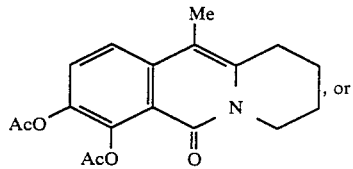, or

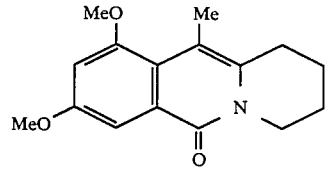

wherein Ac represents acetyl and Me represents CH$_3$.

14. A compound represented by the formula

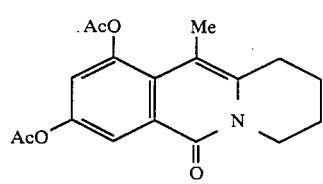

15. A pharmaceutical composition which comprises an anti-allergy effective amount of a compound having structural formula 1.0 as defined in claim 1, in combination with a pharmaceutically acceptable carrier.

16. A method for treating allergy in a mammal comprising administering to said mammal an anti-allergy effective amount of a compound as claimed in claim 1.

17. A method for treating inflammation in a mammal comprising administering to said mammal an antiinflammatory effective amount of a compound as claimed in claim 1.

18. A method for treating hyperproliferative skin disease in a mammal comprising administering to said mammal an anti-hyperproliferative amount of a compound as claimed in claim 1.

* * * * *

UNITED STATES PATENT AND TRADEMARK OFFICE
CERTIFICATE OF CORRECTION

PATENT NO. : 4,897,391

DATED : January 30, 1990

INVENTOR(S) : Richard J. Friary

It is certified that error appears in the above-identified patent and that said Letters Patent are hereby corrected as shown below:

Column 2, lines 31-40, formula 1.0 the generalized structure should show the optional double bonds depicted by broken lines

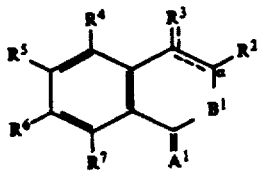

Claim 1, column 29, lines 1-9 in the generalized structure of claim 1 optional double bonds should be shown by lines to $R^2$ and $R^3$ as shown below:

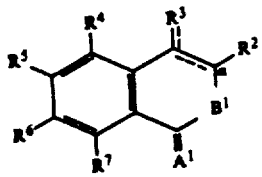

Claim 1, column 29, line 12 the word "optical" should be —optional—.

Claim 1, column 29, line 15, the "?" should be —∝—.

Claim 1, column 29, line 18, the term "(CH$_2$)aN" should be —(CH$_2$)$_a$N—.

Claim 1, column 29, line 31 after "independently" insert —is—.

Claim 1, column 29, line 32 delete "-acyl" and insert —O-acyl—.

UNITED STATES PATENT AND TRADEMARK OFFICE
CERTIFICATE OF CORRECTION

PATENT NO. : 4,897,391

DATED : January 30, 1990

INVENTOR(S) : Richard J. Friary

It is certified that error appears in the above-identified patent and that said Letters Patent is hereby corrected as shown below:

Claim 12, 7th compound, column 30, lines 53-54 the compound name should read: 8, 10, 11-tris(acetyloxy) - 1,2,3,4, tetrahydro-6H-benzo [b] quinolizin-6-one --.

Signed and Sealed this

Twenty-sixth Day of March, 1991

*Attest:*

HARRY F. MANBECK, JR.

*Attesting Officer*     *Commissioner of Patents and Trademarks*